United States Patent [19]

Kutzbach et al.

[11] 4,045,552

[45] Aug. 30, 1977

[54] PROTEASE-FREE PROTEINS, AND METHODS OF MANUFACTURING AND USING THE SAME

[75] Inventors: Carl Kutzbach; Alfred Arens; Gunter Schmidt-Kastner, all of Wuppertal, Germany

[73] Assignee: Bayer Aktiengesellschaft, Germany

[21] Appl. No.: 604,086

[22] Filed: Aug. 13, 1975

[30] Foreign Application Priority Data

Sept. 7, 1974 Germany .............................. 2442995

[51] Int. Cl.² ................................................ A61K 37/48
[52] U.S. Cl. ...................................................... 424/94
[58] Field of Search ............................................ 424/94

[56] References Cited

FOREIGN PATENT DOCUMENTS 2,154,557 5/1973 Germany .............................. 424/94

*Primary Examiner*—Albert T. Meyers
*Assistant Examiner*—Daren M. Stephens
*Attorney, Agent, or Firm*—Jacobs & Jacobs

[57] ABSTRACT

Protease-free proteins, especially protease-free kallikrein, which are prepared by contacting a solution of the protein with a carrier-bound water-insoluble protease inhibitor that does not bind to said protein, and have improved storage stability in solution.

10 Claims, 1 Drawing Figure

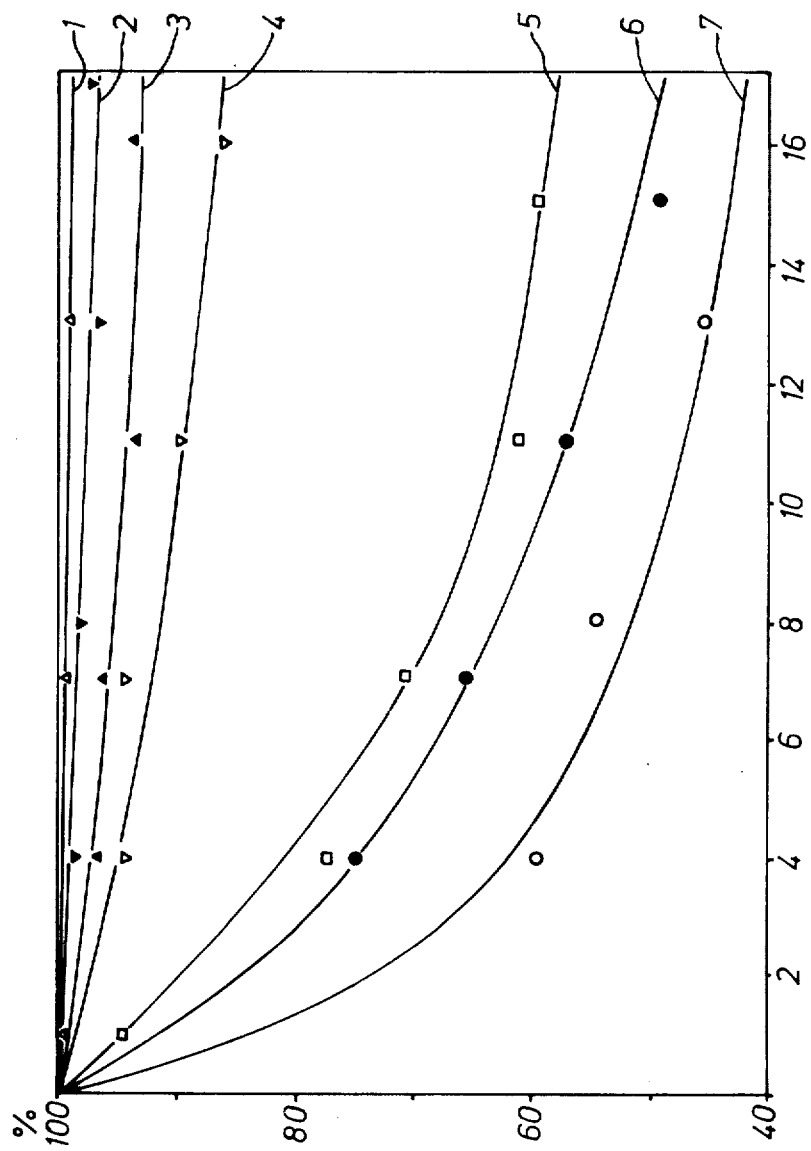

PROTEASE-FREE PROTEINS, AND METHODS OF MANUFACTURING AND USING THE SAME

The present invention relates to protease-free protein, particularly kallikrein, solutions; a process for their preparation; and their use as medicaments.

When kallikrein acts on endogenic kininogen, it liberates the physiologically active kinins (for example kallidine). Kallikrein preparations are therefore used therapeutically [E. K. Frey, H. Kraut and E. Werle, "Das Kallikrein-Kinin-System and seine Inhibitoren" (The Kallikrein-Kinin System and Its Inhibitors), F. Enke, Stuttgart, 1968, page 150 et seq.].

It has already been disclosed that kallikrein can be prepared, for example, from pancreas glands of pigs in accordance wih the process of German Published Specification No. 2,154,557. It is preferably administered orally or by intramuscular or intravenous injection.

Hitherto it has, however, not been possible to prepare injection solutions which can be kept for prolonged periods. The kallikrein solution filled into ampoules was therefore usually brought to a dry form, and hence to the more stable solid form, for example by freeze-drying, and the solid kallikrein was dissolved in a suitable isotonic solution before use.

This procedure is involved and time-consuming, and in addition has the disadvantage that the small, physiologically active amounts of kallikrein can only be freeze-dried in the presence of inert additives acting as structure-forming agents, for example polyvinylpyrrolidone, mannitol, dextran, lactose and others; thus when used therapeutically, undesired foreign substances are administered together with the active compound.

It has also been possible hitherto in principle to achieve stabilization of the solutions of kallikrein by adding to the kallikrein solution suitable inhibitors which do not inhibit kallikrein and thereby inactivate the protease impurities. However, such additions of foreign substances exhibiting biological activity are most undesirable in a medicament.

It is therefore an object of the invention to provide a process for producing very pure solutions of kallikrein, free from foreign additives, which are stable for prolonged periods.

This is accomplished by the present invention by the provision of protease-free kallikrein. Desirably, the protease content should be as low as possible, with good results being obtained at a protease content of not more than 0.011 U/mg, e.g. from 0.004 to 0.011 U/mg, for kallikrein having an activity of 1000–1300 KU/mg.

The present invention is based on the discovery that even the purest preparations of kallikrein which have hitherto been disclosed still contain traces of proteolytic enzymes in an order of magnitude of $\leq 1\%$ and that, surprisingly, there is a direct relationship between the protease content of various kallikrein preparations and their stability in solution. The loss in kallikrein activity on storing the solution is, as we have found, attributable to a destruction of the kallikrein molecule by proteases.

Although protease impurities can be removed by the relatively difficult conventional purification processes, for example ion exchange chromatography, the conventional processes are often accompanied by great losses of kallikrein activity. Surprisingly it is possible, in accordance with a further feature of the invention, to stabilize kallikrein by treating kallikrein solutions with a carrier-bound water-insoluble protease inhibitor which does not bind to kallikrein.

In this simple and elegant manner, highly pure kallikrein solutions can be prepared which are stable for longer periods than conventional kallikrein solutions without having to add stabilizers and without first having to lyophilize the kallikrein and dissolving it, only shortly before use, to form a suitable isotonic solution.

Suitable inhibitors for use in the present invention are, in particular, naturally occurring inhibitors having a polypeptide structure, for example a mixture of different protease inhibitors from soya bean or from potato, or the purified trypsin inhibitor from soya bean (Kunitz) or purified protease inhibitors from potato or the ovomucoid inhibitor from hen's egg. In particular, the protease inhibitor mixture from potato is an easily accessible material which is very suitable for the purpose according to the invention.

With the aid of the process according to the invention, it is in principle also possible to remove proteases from solutions of natural substances other then kallikrein; for this purpose, in addition to the inhibitors already mentioned, the Kunitz trypsin inhibitor from cattle organs is, in particular, also suitable.

Such other solutions, to which the process according to the invention can be applied analogously are, in particular, solutions of enzymes, for example asparaginase, carboxypeptidase A and B, zymogens, peptide hormones, for example oxytocin, vasopressin, insulin and glucagon, as well as blood plasma and purified fractions prepared therefrom.

The above-mentioned inhibitors are bound to water-insoluble carriers in accordance with general processes known to those skilled in the art. However, in each individual case the optimum conditions must be determined by experiment.

For example, the inhibitors mentioned, or further inhibitors with similar properties, can be bound, according to German Published Specification 1,907,365, to cross-linked agarose, such as "Sepharose"[R], by first activating the latter with BrCN. In the same way, the inhibitors can also be bound to other carriers containing hydroxyl groups, for example to cellulose or cross-linked dextran, such as "Sephadex"[R].

Alternatively, it is possible first to bind a low molecular weight amino compound with BrCN to one of the above-mentioned carriers so that a derivative having a free amino or carboxyl group is produced, to which the inhibitor is bound by means of a water-soluble carbodiimide. The low molecular amino compound used for this purpose is, for example, 1,6-diaminohexane or 6-aminocaproic acid.

Furthermore, the inhibitors can be bound to polymers containing carboxylic acid anhydrides, for example to a copolymer of tetraethylene glycol dimethacrylate and maleic anhydride according to German Published Specification No. 2,215,539, or a copolymer of tetraethylene glycol dimethacrylate, maleic anhydride and a hydrophilic monomer, for example methacrylic acid, according to German Published Specification No. 2,215,687.

Further processes which can be used for the preparation of water-insoluble carrier-bound inhibitors have been summarized, for example, by P. Cuatrecasas and Ch. B. Anfinsen (Annual Reviews of Biochemistry, 1971).

The treatment, according to the invention, of the highly purified, optionally crystallized, kallikrein, prepared according to German Published Specification No. 2,154,557 or other suitable processes, with the carrier-bound inhibitors is preferably carried out in dilute aqueous solution containing about 1 to about 50,000 KU/ml of kallikrein at a pH value of about 5.0 to about 8.0. The solution can contain the usual neutral salts or buffer salts in concentration of up to about 1.0 M, for example alkali metal or ammonium chlorides, acetates, formates, carbonates, citrates, phosphates and the like. Preferably, the treatment is carried out in a salt-free solution or an optionally isotonic solution containing NaCl or sodium acetate, so that the stabilized solution can be used directly, without desalination, for the production of therapeutic preparations. The solution can furthermore contain suitable added preservatives, for example ethyl-mercuric thiosalicylate or benzyl alcohol.

The treatment of the aqueous kallikrein solution with the carrier-bound inhibitor may be carried out by stirring the carrier-bound inhibitor into the kallikrein solution and removing it, after a reaction time of at least about 10 minutes, by filtration or centrifuging. However, the method wherein the carrier-bound inhibitor is introduced into a chromatography tube and the kallikrein solution is allowed to run through it is preferred.

The requisite amount of carrier-bound inhibitor depends on the inhibitor used and the degree of protease contamination of the solution to be treated. The carrier-bound inhibitors can be regenerated by treatment with dilute acids or with acid buffers, and can be used several times.

The success of the treatment of the kallikrein solution with carrier-bound inhibitors is shown by the reduced protease content and the improved stability.

The protease content is measured by titrating the aminoacid carboxyl groups liberated by the action of the protease-containing kallikrein solution on casein. A 6% strength solution of casein (according to Hammersten, Merck 2242) in 0.1 N KCl is used and the titration is carried out with 0.02 N KOH at pH 9.5 and 30° C. 1 protease unit is defined as the amount of enzyme which splits 1 micro-equivalent of peptide bond in 1 minute under the conditions indicated.

In order to reduce the period of observation, the stability of the kallikrein preparations was tested at 40° C. The kallikrein activity is determined by measuring the hydrolysis of N-benzoyl-L-arginine ethyl ester as a titrimetric test in the embodiment standardized by the F.I.P. (Federation Internationale Pharmaceutique). 1 F.I.P. unit is defined as the amount of kallikrein which splits 1 micromol of N-benzoyl-L-arginine ethyl ester in one minute at pH 8.0 and 25° C. The calculation to convert the result to the customary kallikrein units (KU), according to the definition of Frey, Kraut and Werle, is made by multiplying by a factor of 6.37.

The kallikrein solutions prepared by the process according to the invention can, in a manner which is in itself known and in dosages which are in themselves known, be employed directly as vasodilators and be administered by intramuscular or intravenous injection for treatment of peripheral vascular and coronary artery disease. The protease-free stable kallikrein solutions according to the invention are conveniently stored in the form of ampoules.

The present invention is illustrated by the drawing, which is a series of graphs showing the stability of various kallikrein preparations from the Examples which follow. The activity of each kallikrein preparation, in percent of the initial activity (= 100), is plotted on the ordinate and the storage time of the kallikrein preparations, at 40° C in days, is shown on the abscissa. The individual curves in the drawing denote the following:

Curve 1: treated kallikrein from Example 1b
Curve 2: treated kallikrein from Example 6
Curve 3: treated kallikrein from Example 5c
Curve 4: treated kallikrein from Example 3b
Curve 5: untreated kallikrein from Example 2
Curve 6: treated kallikrein from Example 10
Curve 7: untreated kallikrein from Examples 1 and 3 to 10.

The invention is explained in more detail by the Examples which follow, but is not restricted to the procedures presented in the Examples. All the kallikrein units (KU) indicated in the Examples which follow are units according to Frey, Kraut and Werle.

EXAMPLE 1 a. Binding soya trypsin inhibitors to "Sepharose".

10 ml of "Sepharose" 4 B (Pharmacia), a cross-linked agarose, were washed with water, suspended in 20 ml of water and activated for 5 minutes with 550 mg of BrCN in 20 ml of water at pH 11 to 11.5. The product was filtered off on a glass frit and briefly washed with ice-cold 0.1 M NaHCO$_3$ solution. The activated "Sepharose" was immediately suspended in 30 ml of cold 0.1 M NaHCO$_3$ solution and 100 mg of soya trypsin inhibitor (highest purity, Serva) were added. The mixture was stirred for 24 hours at about 4° C. The carrier-bound inhibitor was then filtered off on a frit and washed with 0.1 M borate of pH 8.0, 0.1 M acetate of pH 4.0 and water.

Spectrophotometric determination of the non-bound inhibitor in the filtrate and wash water indicated 94 mg had been bound.

b. Treatment of kallikrein with carrier-bound soya trypsin inhibitor.

50 mg of kallikrein having a specific activity of 1,013 KU/mg and protease content of 0.065 U/mg were dissolved in 10 ml of H$_2$O and filtered through a column (0.9 × 15 cm) containing 10 ml of the carrier-bound inhibitor prepared according to Example 1a. The filtrate containing kallikrein was lyophilized and gave 49 mg containing 1,010 KU/mg (= 97.5% of theory) and having a protease content of 0.005 U/mg.

The comparison of the stability of starting material (curve 7) and treated product (curve 1) is shown in the drawing.

EXAMPLE 2

700 mg of kallikrein having a specific activity of 1,080 KU/mg and a protease content of 0.058 U/mg were dissolved in water and filtered through 22 ml of a carrier-bound soya trypsin inhibitor prepared according to Example 1a. After freeze-drying, the filtrate gave 695 mg having a specific activity of 1,050 KU/mg (= 95% of theory) and a protease content of 0.005 U/mg.

EXAMPLE 3 a. Binding ovomucoid inhibitor to "Sepharose".

Following the procedure of Example 1a, 10 ml of "Sepharose" were activated with BrCN and reacted with 100 mg of ovomucoid (Worthington). 78 mg of ovomucoid were bound.

b. 50 mg of kallikrein (specific activity: 1,013 KU/mg; protease: 0.065 U/mg) were dissolved in 0.02 ammonium acetate of pH 6.0 and the solution was filtered through a column (0.9 × 15 cm) containing 10 ml of the carrier-bound inhibitor prepared according to Example 3a. The kallikrein yield in the filtrate was 92% of theory. A sample was desalinated over "Sephadex G-25" and lyophilized. Specific activity: 980 KU/mg; protease: 0.008 U/mg. Curve 4 shows the stability of the treated kallikrein and curve 7 the untreated.

EXAMPLE 4 a. Preparation of inhibitor mixture from potato.

Washed potatoes were comminuted and suspended in a mixture of 0.95 kg of methanol, 0.375 kg of distilled water and 0.025 kg of 60% strength perchloric acid per kg of potato. Undissolved material was separated off on a filter press. The perchloric acid was neutralized by addition of potassium carbonate until the pH is 5.5. Potassium perchlorate which had precipitated was filtered off. The filtrate was concentrated by evaporation in vacuo, then dialyzed and finally freeze-dried. About 450 mg of inhibitor/kg of potato were obtained.

b. Binding of inhibitor mixture from potato to "Sepharose".

160 mg of an inhibitor preparation according to Example 4a were reacted, analogously to the procedure of Example 1a, with 40 ml of BrCN-activated "Sepharose". 139 mg of inhibitor were bound.

c. 50 mg of kallikrein (specific activity 1,013 KU/mg; protease: 0.065 U/mg) were dissolved in 0.05 M ammonium acetate of pH 6.0 and the solution was filtered through a column (0.9 × 15 cm) containing 10 ml of the carrier-bound inhibitor prepared according to Example 4b. The kallikrein yield in the filtrate was 89% of theory. A desalinated and lyophilized sample had a specific activity of 1,010 KU/mg and a protease content of 0.004 U/mg.

EXAMPLE 5 a. Preparation of purified protease inhibitor from potato.

80g of a protease inhibitor mixture from potato, prepared according to Example 4a, were applied to a column (9.5 × 110 cm) containing 7 l of carboxymethyl-"Sephadex" C-50 in 0.01 M ammonium acetate of pH 4.5. The column was then first washed with 2 l of the initial buffer and thereafter eluted with a linear concentration gradient of up to 1 M ammonium acetate of pH 5.4. Fractions of high inhibitor activity against pancreas proteases were combined, concentrated, dialyzed and freeze-dried. An enriched inhibitor preparation was obtained in about 12% by weight yield relative to the crude preparation employed, or 55 mg/kg of potato.

b. Binding of purified protease inhibitor from potato to "Sepharose".

160 mg of a purified inhibitor preparation from potato were reacted with 40 ml of "Sepharose" in the same manner as described in Example 4b. 146 mg of the inhibitor were bound.

c. In the same manner as in Example 4c, 50 mg of kallikrein were treated with 10 ml of the carrier-bound inhibitor prepared according to Example 5b. The yield was 95% of theory, the specific activity was 1,010 KU/mg and the protease content was 0.009 U/mg. Curves 3 and 7 compare the storage stability of the treated and untreated kallikrein.

EXAMPLE 6

4 ml of each of the carrier-bound initiators prepared according to Examples 1b, 3b and 5b were mixed and 50 mg of kallikrein were treated with the mixture analogously to Example 4c. The yield was 96%, the specific activity was 1,000 KU/mg and the protease content was 0.007 U/mg. Curves 2 and 7 compare the storage stability of the treated and untreated kallikrein.

EXAMPLE 7 a. Binding of 1,6-diaminohexane to "Sepharose".

100 ml of "Sepharose" were activated with 15g of BrCN and then reacted with 23.3g of 1,6-diaminohexane. The product was washed with borate buffer of pH 8.5, acetate buffer of pH 4.0 and water. A freeze-dried sample had a nitrogen content of 5.9%.

b. Binding of protease inhibitor from potato to "Sepharose" substituted with 1,6-diaminohexane.

16 ml of the Sepharose derivative according to Example 7a were suspended in 15 ml of water and stirred, after addition of 200 mg of protease inhibitor from potato obtained from Example 5a and 200 mg of ethyl-(3-dimethylamino-propyl)-carbodiimide hydrochloride for 24 hours at pH 4.7. The product was then filtered off and washed with 1 M NaCl and water. 189 mg of inhibitor were bound.

c. 50 mg of kallikrein were treated, as described in Example 4c, with the carrier-bound inhibitor prepared according to Example 7b. The yield was 93% of theory, the specific activity 995 KU/mg and the protease content 0.011 U/mg.

EXAMPLE 8 a. Binding of protease inhibitor from potato to "Sepharose" substituted with 6-aminocaproic acid.

16 ml of "Sepharose" substituted with 6-aminocaproic acid (CH-"Sepharose") were reacted with 200 mg of protease inhibitor from potato as described in Example 7b. 195 mg of inhibitor were bound.

b. 50 mg of kallikrein were treated, as described in Example 4c, with the carrier-bound inhibitor prepared according to Example 8a. The yield was 92% of theory, the specific activity 988 KU/mg and the protease content 0.0095 U/mg.

EXAMPLE 9 a. Preparation of a copolymer of tetraethylene glycol dimethacrylate, methacrylic acid and maleic anhydride.

60g of tetraethylene glycol dimethacrylate, 30g of methacrylic acid, 10g of maleic anhydride and 1g of azoisobutyronitrile are dissolved in 300 ml of acetonitrile. This solution is suspended in 1 l of benzene (boiling point 100–140° C), which contains 5g of a mixture of glycerol monooleate and glycerol dioleate, and polymerized for 22 hours at 60° C.

The polymer beads are filtered off, suspended three times in benzene and twice in petroleum ether (boiling point 30–50° C) and dried in vacuo.

Yield: 94g
Bulk volume: 44 ml/g
Swelling volume in water: 5.5 ml/g
Specific surface area: 6.6 m²/g
Acid content after saponification of the anhydride groups: 4.3 milliequivalents/g.

b. Binding of protease inhibitor from potato.

10g of a copolymer according to Example 9a were washed with 100 ml of acetone and then suspended in 880 ml of water. 40 ml of 0.1 M triethylamine were added and the pH was adjusted to 6.2 with 0.1 M acetic acid in exactly 1 minute. 1.0g of protease inhibitor from potato according to Example 5a was then added and the pH was kept at 6.2. After 24 hours, the carrier-bound inhibitor was filtered off and washed with 0.1 M sodium borate of pH 8.5, 0.1 M sodium acetate of pH 4.0 and water. 280 mg of inhibitor were bound.

c. 50 mg of kallikrein were treated, as described in Example 4c, with 10 ml of the carrier-bound inhibitor prepared according to Example 9b. The yield was 88% of theory, the specific activity 1,005 KU/mg and the protease content 0.011 U/mg.

The results of the treatment of kallikrein with the various carrier-bound inhibitors are summarized in the Table which follows.

TABLE

Result of the treatment of kallikrein with carrier-bound inhibitors

| Example | Starting material | | Treated kallikrein | | |
|---|---|---|---|---|---|
| | KU/mg | Protease-U/mg | Yield, % | KU/mg | Protease-U/mg |
| 1b | | | 97.5 | 1,010 | 0.005 |
| 3b | | | 92 | 980 | 0.008 |
| 4c | | | 89 | 1,010 | 0.004 |
| 5c | 1,013 | 0.065 | 95 | 1,010 | 0.009 |
| 6 | | | 96 | 1,000 | 0.007 |
| 7c | | | 93 | 995 | 0.011 |
| 8b | | | 92 | 988 | 0.0095 |
| 9c | | | 88 | 1,005 | 0.011 |
| 2 | 1,080 | 0.058 | 95 | 1,005 | 0.005 |

EXAMPLE 10 — COMPARISON EXAMPLE

Chromatography of highly purified kallikrein on DEAE-Sephadex A-50

100 mg of kallikrein having a specific activity of 1,013 KU/mg and a protease content of 0.065 U/mg were dissolved in 50 ml of sodium acetate buffer of pH 5.0, 12 mS/cm and charged onto a 2.5 × 40 cm column of DEAE-Sephadex A-50 in the same buffer. The column was rinsed with 300 ml of sodium acetate of pH 5.0, 14 mS/cm and eluted with a linear gradient of 300 ml each of sodium acetate pH 5.0 14 mS/cm and 0.5 M respectively.

The active fractions of the eluate (210 ml) were combined, concentrated to 20 ml by ultrafiltration, desalinated on a column of Sephadex G-25 and freeze-dried.

Yield: 61 mg with 1,320 KU/mg = 79%

Protease content: 0.014 U/mg

The stability of this preparation is shown as curve 6 in the drawing.

What is claimed is:

1. A method of removing protease from kallikrein, comprising contacting a solution of the kallikrein with a carrier-bound water-insoluble polypeptide protease inhibitor that does not bind to said kallikrein, and recovering a protease-free kallikrein.

2. A method according to claim 1, wherein the protease inhibitor is a potato, soya bean, or ovomucoid protease inhibitor.

3. A method according to claim 2, wherein the protease inhibitor is bound to a cross-linked agarose, cellulose, a cross-linked dextran, or a polymer containing carboxylic anhydride groups.

4. A method according to claim 1, wherein the solution is a salt-free or blood-isotonic solution.

5. A method according to claim 1, wherein an aqueous kallikrein solution containing from about 1 to about 50,000 KU/ml at a pH of from about 5.0 to about 8.0 is contacted with said carrier-bound protease inhibitor.

6. A method according to claim 5, wherein said aqueous solution is salt-free or blood-isotonic.

7. A method according to claim 5, wherein the carrier-bound protease inhibitor is in a chromatography tube and said aqueous solution is introduced into said tube and allowed to run through the tube.

8. Kallikrein having an activity of about 1000 to 1300 KU/mg and a protease content of about 0.004 to about 0.011 U/mg produced by the method of claim 1.

9. Kallikrein according to claim 8 in the form of a sterile or isotonic aqueous solution.

10. An aqueous solution according to claim 9 which contains from 1 to 50,000 KU/ml of kallikrein.

* * * * *